(12) United States Patent
Matias et al.

(10) Patent No.: US 11,779,673 B2
(45) Date of Patent: Oct. 10, 2023

(54) AIRBORNE VIRUS, FUNGI, BACTERIA AND OTHER MICROORGANISMS AIR STERILIZATION SYSTEM

(71) Applicant: Airfree Produtos Electronicos S.A., Lisbon (PT)

(72) Inventors: Carlos Jose Duarte Matias, Lisbon (PT); Daniel Oliveira Duarte Matias, Sao Paulo (BR); Raphael de Oliveira Duarte Matias, Sao Paulo (BR)

(73) Assignee: AIRFREE PRODUTOS ELECTRONICOS S.A.

( * ) Notice: Subject to any disclaimer, the term of this patent is extended or adjusted under 35 U.S.C. 154(b) by 150 days.

(21) Appl. No.: 17/343,158

(22) Filed: Jun. 9, 2021

(65) Prior Publication Data

US 2022/0395603 A1    Dec. 15, 2022

(51) Int. Cl.
*A61L 9/16* (2006.01)
*B01D 46/00* (2022.01)
*A61L 9/014* (2006.01)
*B01D 46/42* (2006.01)

(52) U.S. Cl.
CPC ............ *A61L 9/16* (2013.01); *A61L 9/014* (2013.01); *B01D 46/0028* (2013.01); *B01D 46/0036* (2013.01); *B01D 46/0039* (2013.01); *B01D 46/429* (2013.01); *B01D 46/4263* (2013.01); *A61L 2209/14* (2013.01); *A61L 2209/16* (2013.01); *A61L 2209/22* (2013.01); *B01D 2273/30* (2013.01); *B01D 2279/35* (2013.01); *B01D 2279/65* (2013.01)

(58) Field of Classification Search
CPC ........ A61L 9/16; A61L 9/014; A61L 2209/14; A61L 2209/16; A61L 2209/22; B01D 46/0028; B01D 46/0036; B01D 46/0039; B01D 46/4263; B01D 46/429; B01D 2273/30; B01D 2279/35; B01D 2279/65
See application file for complete search history.

(56) References Cited

U.S. PATENT DOCUMENTS

| | | | |
|---|---|---|---|
| 4,877,990 | A | 10/1989 | Fiorenzano, Jr. |
| 5,874,050 | A | 2/1999 | Matias |
| 7,332,140 | B2 | 2/2008 | Matias |
| 8,699,866 | B2 | 4/2014 | Lee et al. |
| 2017/0128607 | A1* | 5/2017 | Lee .......................... A61L 9/122 |

* cited by examiner

*Primary Examiner* — Gabriel E Gitman
(74) *Attorney, Agent, or Firm* — Ware, Fressola, Maguire & Barber LLP

(57) ABSTRACT

The formation of sterilization tubes by plates with parts that match in whole or in part, that when assembled together form ducts, passages, channels, or tubes in a mass or block of heat resistant material. The size of the block may be reduced by forming the ducts as curved passages or tubes that will keep or increase the length of the tube while keeping the same or more exposure time while the gas is passing through. If the length of the curved duct is the same as a straight tube would have been, the overall size of the assembly may be reduced from what it otherwise would have been. If the curved length is made longer while the size of the assembly is kept the same, the exposure time is increased for a more effective sterilization.

21 Claims, 9 Drawing Sheets

AIRBORNE VIRUS, FUNGI, BACTERIA AND OTHER MICROORGANISMS AIR STERILIZATION SYSTEM

BACKGROUND OF THE INVENTION

The invention is generally directed to an improved air sterilization device that works with ducts to contain intense heat that effectively destroys micro-organisms such as virus, mold, bacteria, pet dander allergens, and dust mite and other insect allergens, avoids mildew formation and cross contamination, providing healthier environments and preserve food items. It should be realized that the invention is applicable to gases other than air so that in general it relates to improvements in a gas sterilization system.

In U.S. Pat. No. 4,877,990 there is shown an air sterilization device that consists of a refractory ceramic mass or block (of height 70 mm) of zirconium dioxide ($ZrO_2$) and quartz ($SiO_2$) and consisting of a relatively high number (e.g. fifty-six) of vertically extending high thermal gradient ducts or 2 mm diameter bores designed as a function of an air volume to be processed. Heating elements in the form of NiCr resistive wire filaments having a resistance of 100 ohm/meter are placed in the small diameter ducts, connected in series (4.5 meters), and energized with rectified current from a 110 volt home outlet to dissipate 24.4 Watts. Room air will circulate upwardly through the ducts by convection and will become sterilized by energy dissipated by the Joule heating effect wherein a high thermal gradient is produced in the interior of the ducts (220° C.) during the traverse through the ducts. Spread out over fifty-six ducts, each duct will dissipate 0.38 Watt. With a volume of $2.2 \times 10^{-7}$ cubic meter, the 0.38 Watt of power will raise the temperature to at most 400° C. under a room condition of 24° C. and 80% relative humidity.

The previous U.S. Pat. No. 5,874,050 A of the applicant hereof discloses a straight tube full of ducts easily achieved by means of extrusion which proved its efficiency in the past years in several countries including the USA.

U.S. Pat. No. 7,332,140 B2 of the same applicant discloses another more flexible version of the technology thus achieving the same air sterilization efficiency, allowing the gas to be sterilized either inside or outside the device where the technology is implemented.

SUMMARY OF THE INVENTION

The present application answers the need for an improved air sterilization system which can be utilized by itself or coupled with other devices but with the possibilty of much smaller external dimensions. The previous US Patents of the present applicant did not offer the possibility of external size reduction due to the use of straight ducts.

The invention is thus in one aspect directed to an improvement to the current air sterilization system from the same applicant, where the sterilizing ducts are no longer straight but with at least one curve in any direction in order to internally maintain or exceed the length of each straight duct yet with the same or increased air residence time within said ducts but reducing at the same time the external size of the mass within which the ducts reside e.g. ceramic block mounted within an assembly while maintaining the same or more air residence time beyond that necessary to destroy airborne microorganisms carried by the air convection continuous flow or in some cases also powered by a fan or equivalent. The concept of the new invention is aimed to reduce the external dimensions of the formed assembly of the ceramic ducts or even increase the size and number of ducts being assembled together, allowing at the same time different configurations for new air sterilizer devices that might be smaller or larger depending on the quantity of ducts formed. The new invention will sterilize the air by a high temperature such as 200° C. inside the heated ducts with minimum heat contribution to the room within which the assembly resides with the objective of drastically reducing its airborne micro-organisms and to avoid formation of organic smells, fungi, mold and destroy viruses, bacteria.

Accordingly, it is an object of the invention to provide an improved sterilization system for standalone, wall mounted, or inserted small and large devices.

Another object of the invention is to provide flexibility in the size and shape of the formed ducts that are shaped for heating air flowing through the ducts during the process of the air sterilization.

Yet another object is to provide a way to provide closely spaced ducts that do not have to be formed into a unitary mass such as ceramic. Ceramic blocks of this kind when made by extrusion for instance are subject to the ducts blending with each other when placed too closely. This is avoided according to another aspect of the present invention by assembling the block from plates with the ducts pre-formed in the surfaces of the plates. For instance, a non-straight, curved, or bent half-duct is pre-formed in the surface of one plate, and a mirror image of that half-duct may be formed in the surface of a matching plate for alignment when stacked into a two-plate section of the block. Of course, it is conceivable that plate with a half-duct formed therein may be matched with a completely flat plate to form a duct with only the shape of a half-duct for instance with a half-circle, half-oval, half-square, half-rectangle, or some other half-shape cross-section.

This way of design of a ceramic block as an assembly of plates also provides design flexibility because the size of the assembly may be chosen without undue design effort. By having a large number of plates on hand, the overall size of the block can be chosen with a great degree of convenience not possible in the prior art where selection of the size of a unitary block and ducting necessarily involves additional pre-production design steps as well as manufacturing of the block of the selected size and ducting.

Still a further object of the invention is to provide an improved air sterilization system coupled to an optional activated carbon block or similar components to capture chemicals and VOCs not destroyed by heat and the optional addition of a fan to enhance the air flow through such a carbon block or similar component and the air sterilizing assembly.

Yet still a further object of the invention is to provide an improved air sterilization and filtering system in which the air sterilization assembly is coupled to a filter or electrostatic filter to capture airborne particles.

Yet another object of the invention is to provide a compact improved air sterilization system to be used or attached to automobiles, other types of vehicles, furniture, home appliances, hanging, wall or table lamps, wall mounted or stand-alone, in which the air in a restricted volume is to be purified with the viruses and bacteria killed, and mold avoided.

Still other objects and advantages of the invention will, in part, be evident and will, at least in part, be apparent from the specification.

According to a first aspect of the present invention, a sterilization system for the sterilization of air in one or more ducts is formed by stacking at least two plates, each plate having a half duct with at least one engraved curve, wherein the at least two plates stacked together form a stacked plate pair that together form at least one duct resulting in an air sterilization assembly with said at least one duct for each air sterilization assembly, each duct having at least one heating element residing therein that when supplied with an electric current heats air within the duct to over 100° C. before the air escapes by convection from inside the duct.

Further, the sterilization system according to the first aspect of the present invention is provided such that air flows into the duct by air convection when a plurality of air sterilization assemblies reside in an air sterilization apparatus that is placed in a base having a bottom inlet at a lower level under the duct and a top outlet at an upper level above the duct allowing the hot air to exit freely upwards generating a negative pressure at the bottom inlet forcing the contaminated air upwards into the duct and out through the top outlet in an endless and constant flow of air.

Further still, the sterilization system according to the first aspect of the present invention, the hot air exiting the duct is cooled down by means of a heat interchange system by contact with colder surfaces or by other cooling means.

In further accord with the first aspect of the present invention, the open channel has at least one curve engraved therein so that when assembled together with a similarly curved open channel in the facing plate the duct is formed in full.

In still further accord with the first aspect of the present invention, a fan is coupled to enhance air movement in the sterilization system in order to improve sterilized air production. The fan allows the sterilization system to operate horizontally, vertically, or inclined.

In still further accord with the first aspect of the present invention, the sterilization system is incorporated into a ventilation duct in a ventilation system for a space in an ediface, an ediface wall, or room of a building.

In still further accord with the first aspect of the present invention, the air sterilization assembly is contained within an insulated cover to inhibit radiation of heat outside the assembly so as to concentrate heat inside the at least one duct.

In still further accord with the first aspect of the present invention, at least one filter or particle remover is coupled to the air sterilization assembly.

In still further accord with the first aspect of the present invention, the sterilization system is monitored and operated by means of wireless communication.

According to a second aspect of the present invention, a plate comprising a ceramic or equivalent insulating material is for assembly adjacent a facing plate as an assembled pair of plates to form a mass or block for the sterilization of air in a duct formed in the assembled pair of plates, the plate having an open channel in a surface of the plate such that when the plate and the facing plate are assembled face-to-face the open channel forms the whole or at least a part of the duct, wherein a heating element residing in the duct that when energized heats air within the duct to over 100° C. before the heated air escapes by convection from inside the at least one duct.

In further accord with the second aspect of the present invention, the assembled pair of plates is attached to an interior of a container of an air sterilization apparatus with at least one air inlet and at least one air outlet.

In still further accord with the second aspect of the present invention, the open channel has at least one curve engraved therein so that when assembled together with a similarly curved open channel in the facing plate the duct is formed in full. The invention accordingly comprises the features of construction, combination of elements, arrangement of parts, combination of steps and procedures, all of which will be exemplified in the constructions and processes hereinafter set forth and the scope of the invention will be indicated in the claims.

BRIEF DESCRIPTION OF THE DRAWINGS

For a fuller understanding of the invention, reference is made to the following description taken in connection with the accompanying drawings, in which:

FIG. 4B shows an edge view of the embodiment of the wired plate of FIG. 4A being joined to another plate with the wire threaded in between.

DETAILED DESCRIPTION OF EMBODIMENTS

Figure 1A:
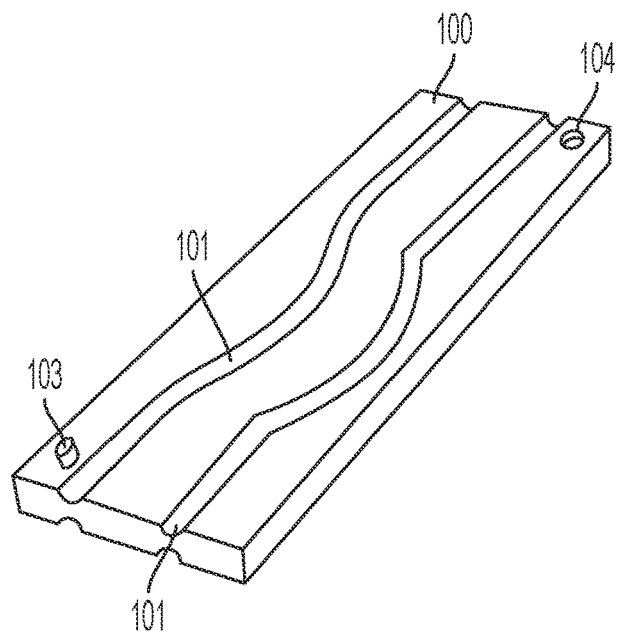
FIG. 1A shows one plate (100) containing a pair of "S" shaped half ducts (101), one assembling dowel or pin 103 and one dowel hole or pin groove 104.
Figure 1B:
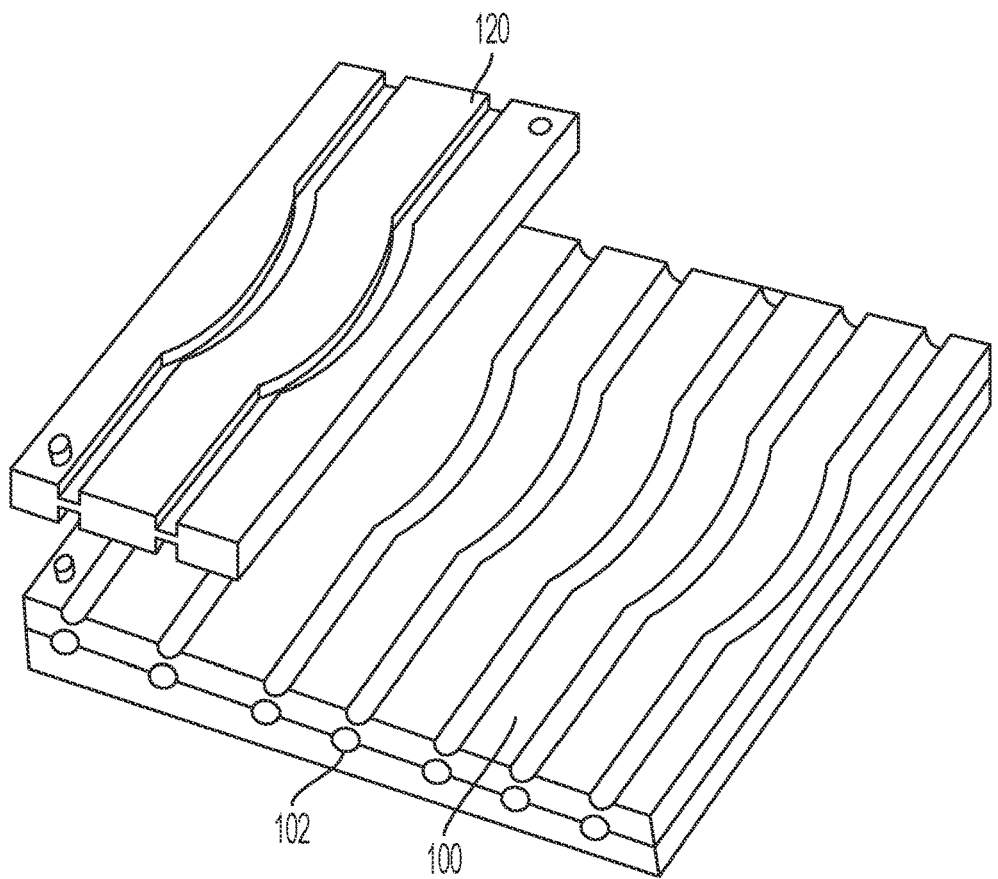
FIG. 1B shows in the top part a plate 120 similar to the plate 100 of FIG. 1A except with rectangular half ducts and shows in a bottom part a pair of mating plates that are larger than the plate 100 of FIG. 1A, each with seven ducts on each side.
Figure 1C:
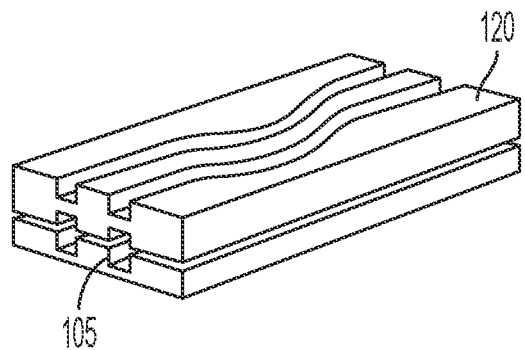
FIG. 1C shows two of the plates 120 shown in the top part of FIG. 1B being assembled to form a structure with ducts 105.
Figure 2:
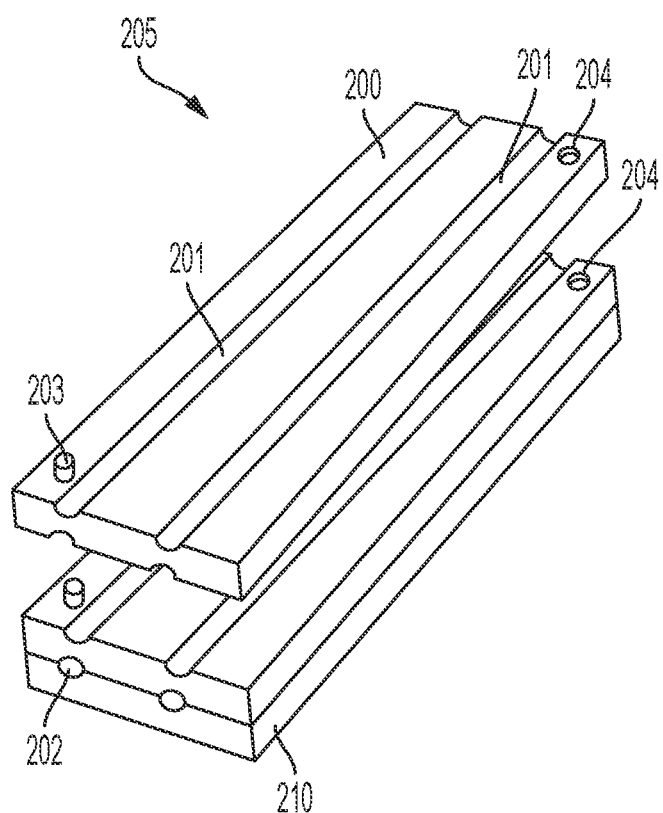
FIG. 2 shows one plate (200) containing a pair of straight shaped half ducts (201), one assembling dowel pin 203 and one dowel pin groove 204 on a visible side being assembled onto a two plate assembly underneath with matching ducts, dowel pins and dowel holes to form a three plate assembly.
Figure 3A:
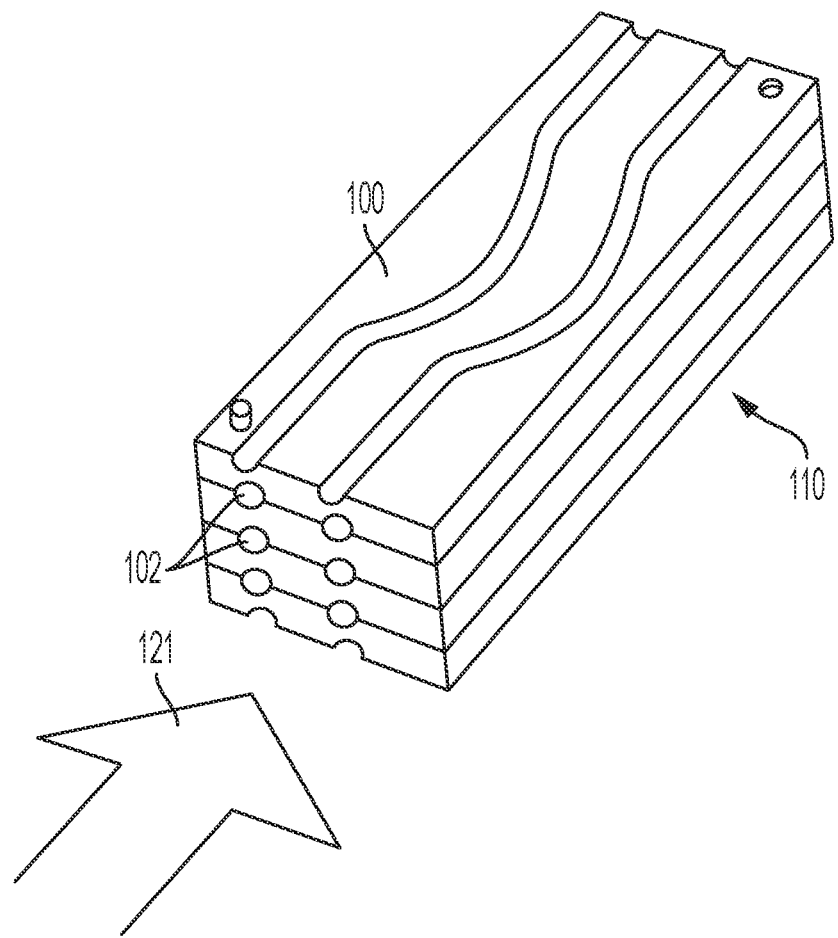
FIG. 3A an isometric view of the new invention (110) with multiple plaques 100 similar to that shown in FIG. 1A assembled together forming "S" shaped ducts (102) creating an air inlet (121) and an air outlet (122) (not seen in the figure at the opposite side of the multiple plaques with "S" shaped ducts (102)).

Reference is first made to FIG. 1A in which one plaque or plate 100 with engrooved half diameter ducts 101, meant to be permanently attached to another facing plaque or plate 100 with mirror image engrooved half diameter ducts to allow for full ducts 102 to be formed as shown in FIGS. 1B and 3A, one optional assembling dowel or pin 103 and one optional assembling dowel or pin receptacle 104, constructed for facilitating permanent alignment of a pair of facing plaques or plates in accordance with an embodiment of the invention. FIG. 1C shows rectangular or square ducts 105 made of plates such as the plate 120 shown in the top of FIG. 1B. The ducts are curved to allow a passage of air that is more circuitous than the straight ducts shown in the embodiment of FIG. 2.

The two plate assemblies shown in FIGS. 1B and 1C constitute examples of basic sterilization systems for the sterilization of a gas such as air in one or more ducts formed by stacking at least two plates, at least one plate having an engraved portion, wherein the at least two plates stacked together form a stacked plate pair that together with the engraved portion of the at least one plate form at least one duct, resulting in a gas sterilization assembly with the at least one duct having at least one heating element residing therein (see FIGS. 4A, 4B & 4C) that when supplied with an electric current heats gas within the duct to over 100° C. before the gas escapes by convection from inside the duct. Thus, the at least one duct is formed at an interface between the stacked plates. Since the plates shown in this example are (without limitation) provided with flat surfaces, the interface is in that case a planar interface with the one or more engraved ducts running along and aligned with a corresponding flat plate surface within the planar interface. The interface is formed by the surfaces of the two plates being in contact with each other such as pressed together so as to make good contact between the plates. FIG. 2 shows that more than two plates may be stacked to form a multi-plate system.

In FIG. 2 plaque or plate 200 is similar to plaque or plate 100 in FIG. 1 with the difference being the ducts 201 are straight. Though the ducts 103 are straight, the assembly of plates shown in FIG. 2 nonetheless retains the advantage of flexible design in that the designer is able to freely choose the number of plates in the stack, given the application.

Thus, FIG. 2 shows a plaque or plate assembly 205 of several plaques or plates 200 in a stack forming full straight ducts 202. Each plaque or plate 200 may include an assembling pin or dowel 203 and a pin or dowel receptacle 204. Although not shown in FIG. 2, another plate 200 may be placed on top of the top plate shown in the figure once it is fixed onto the two plates shown at the bottom. In that case, yet another set of ducts 202 will be formed by means of a four plate stack with three layers of ducts residing in the interfaces formed between the four plates.

Figure 3B:
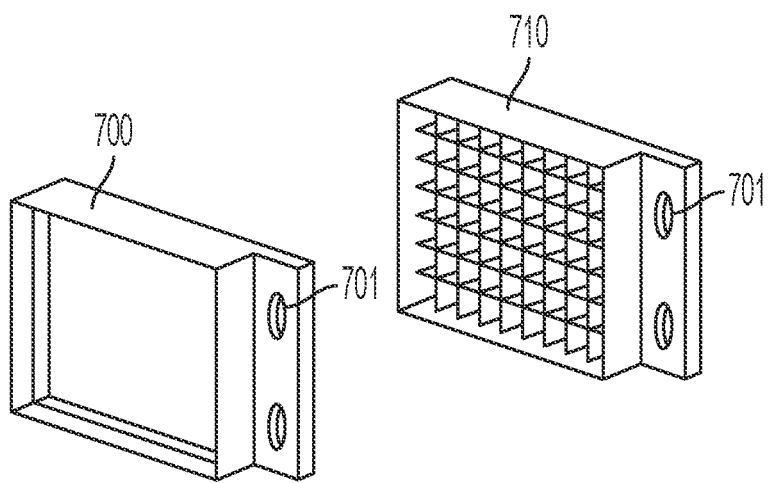
FIG. 3B shows an example of a structure or device 710 for holding an assembly such as the assemblies 110 or 210; the structure or device 700 secures the assembly through any fixing means like screws utilizing holes 701.

FIG. 3A an isometric view of an assembly 110 with multiple plaques or plates 100 similar to that shown in FIG. 1A assembled together forming "S" shaped or curved ducts 102 creating an air inlet 121 and an air outlet (not seen in the figure) at the opposite side of the multiple plaques or plates with the air incoming to the "S" shaped ducts 102 exiting at the other end. The plaques or plates 100 are assembled together to form the assembly 110 where the full ducts 102 are formed. Optional locking devices 700, 710 in FIG. 3B may be provided for stability, i.e., in order to hold together and better secure the assembled plaques or plates in the stacked assembly 110 of plates 100. Holes 701 may be provided to allow attachment of the secured stack of plaques or plates to another structure.

Figure 4A:
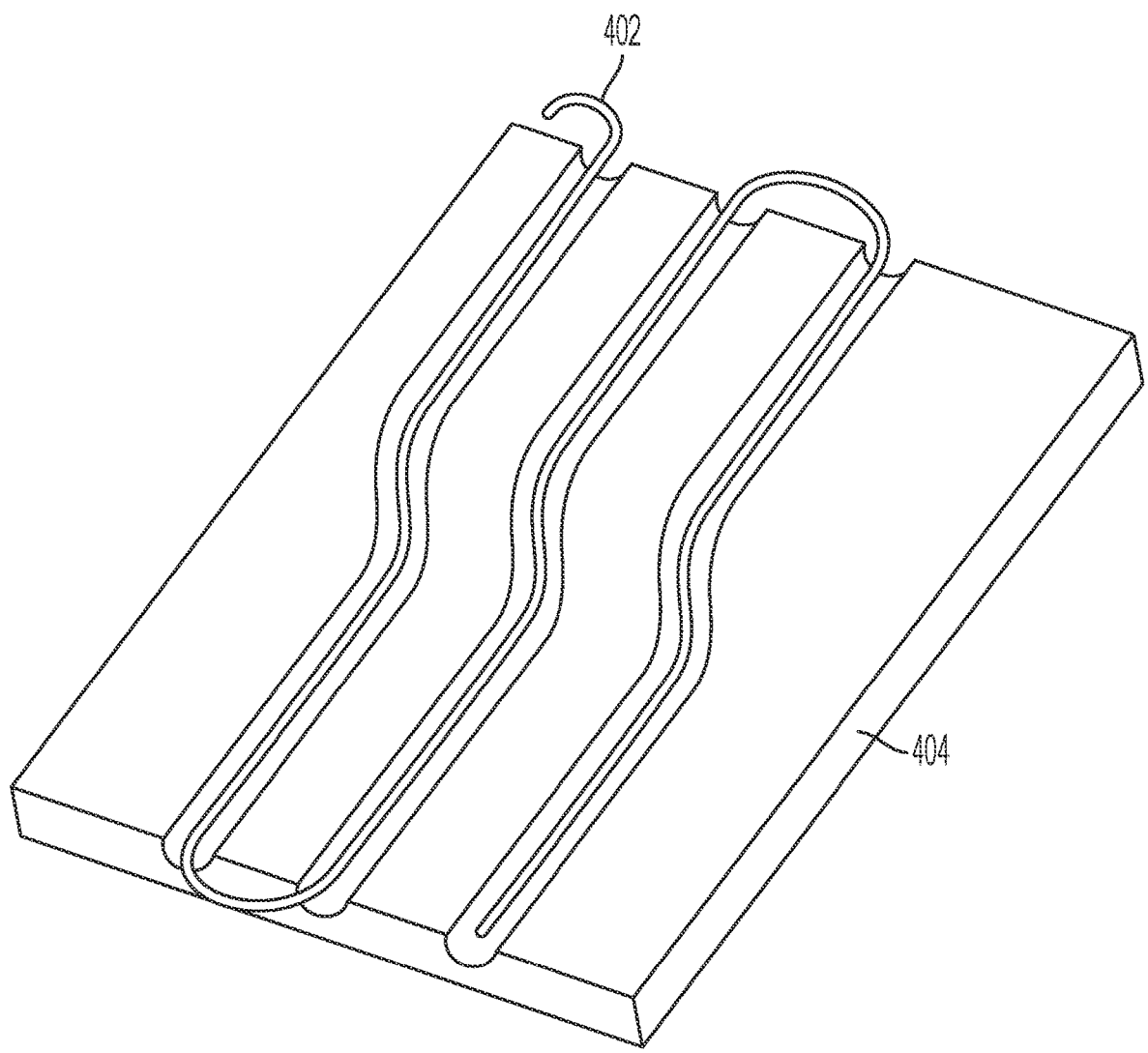
FIG. 4A shows an embodiment of a way to provide an electric wire in the ducts.

FIG. 4A shows an embodiment of a way to provide an conductive wire in the ducts for conducting an electric current. The wire may be a flexible wire that lies loosely in the ducts. In that case, in places along the length of the duct, the wire may or may not lie against the inner wall of the duct. Or, it may be a straight or curved stiff wire, as the case may be, built into a carrier (not shown) set up so the wire does not touch the inner wall at all.

Figure 4B:
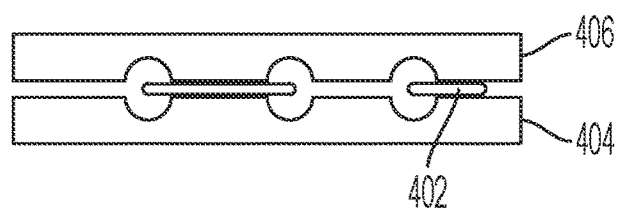

FIG. 4B shows an edge view of the embodiment of the wired plate of FIG. 4A joined to another plate with the wire of FIG. 4A shown threaded in between. As such it may constitute a single length of wire.

Figure 4C:
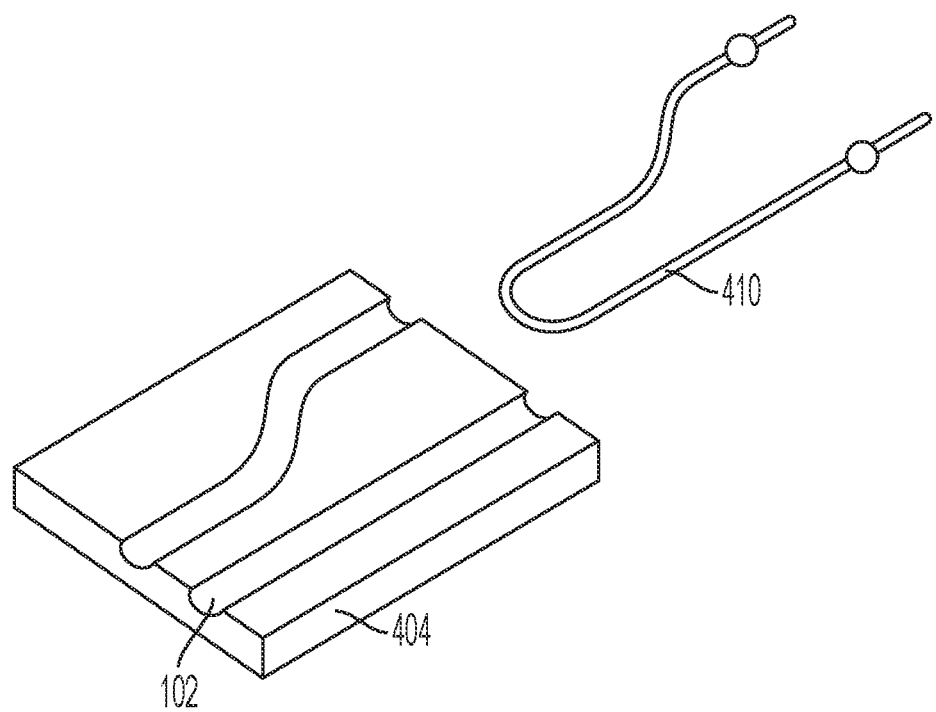
FIG. 4C shows a frame 410 of resistive material in a rigid or stiff form as an optional substitute for a flexible wire approach such as shown by the flexible wire 402 in FIG. 4A.

FIG. 4C shows a plaque or plate 404 and a frame 410 of electrically resistant material substituting for the wire 402 of FIGS. 4A & 4B and configured to meet the ducts 102 format, in this example one straight and one having a bend. The frame 410 may be relatively rigid or stiff as compared to the flexible wire of FIGS. 4A & 4B.

Figures 5, 6:
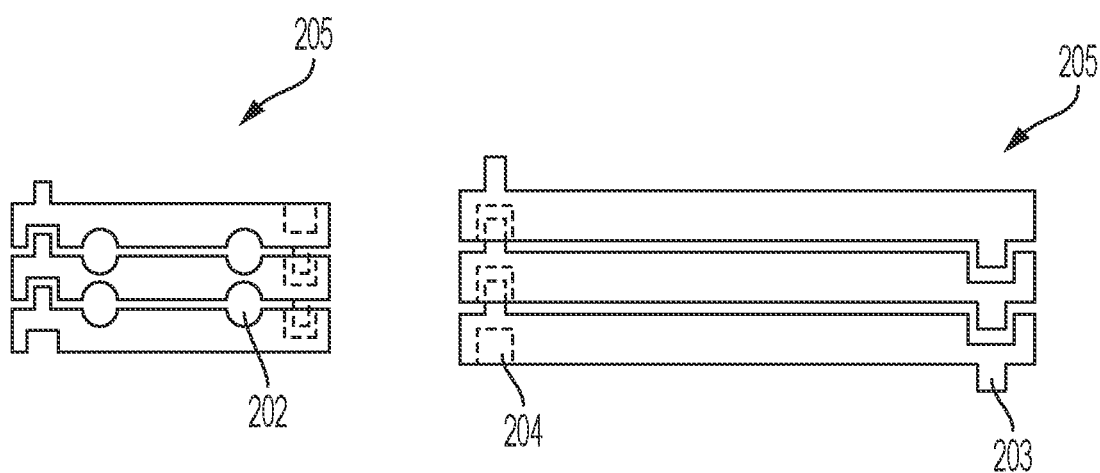
FIG. 5 is a cut away of the structure 205 of FIG. 2 with spaces to better show the assembly, and showing ducts 202.
FIG. 6 is a longitudinal side view of the plates 200 of FIGS. 2 and 5 showing the assembling and securing by optional means of dowel pins 203 and dowel holes, receptacles, or grooves 204.

FIG. 5 shows a transversal cross section of a plaque or plate assembly similar that shown in FIG. 2, except without half ducts 201 on the top plate, showing a cross section of the full ducts 202.

FIG. 6 shows a longitudinal section of the three plaque or plate assembly, similar to that shown in FIG. 2 or 5.

FIG. 7A shows a cutaway perspective view of a slim air purifier 600 with one air inlet 601 and one air outlet 602 where assembly 110 such as shown in FIG. 1B or an assembly 210 such as shown in FIG. 2 is incorporated.

Figure 7:
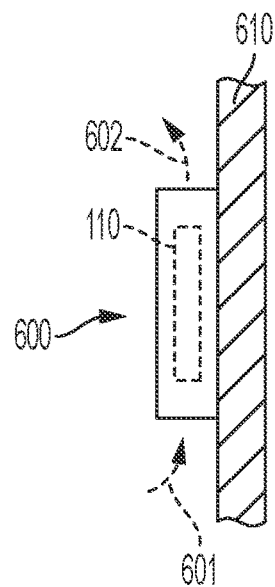
FIG. 7 shows the new invention inside an apparatus, attached to a wall.

As shown in FIG. 7, a plaque or plate assembly such as but not limited to the assemblies shown in FIGS. 1B, 1C, 2, 3A, and 5-6 with multiple half ducts assembled to form full ducts 102, 202 may be included within an air purifier such as the slim air purifier 600 of FIG. 7 and attached to a wall 610 shown in a side view. As can be seen, such an air purifier attached to a wall shows how slim it can be.

Figure 8:
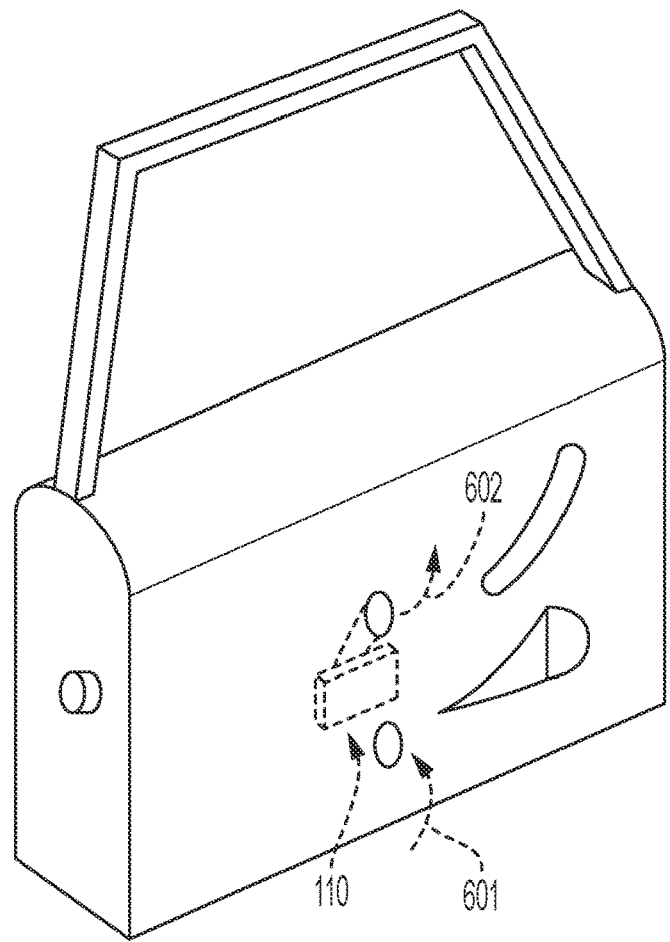
FIG. 8 shows another view of the air purifier of FIG. 8 attached to the internal side of the car door to purify the air of the vehicle.
Figure 9A:
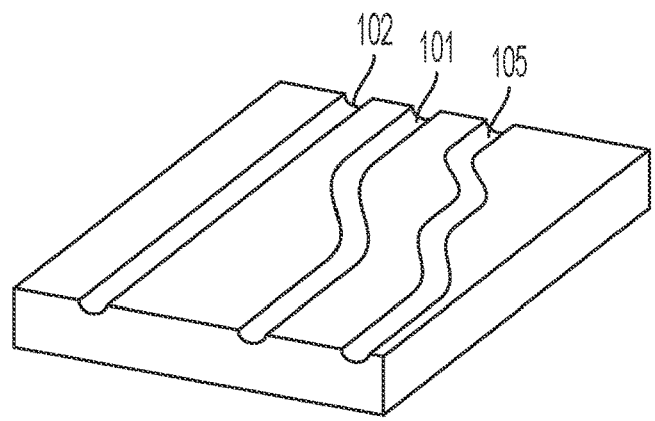
FIG. 9A shows a flat plate with a straight duct, a curved duct with one bend, and a curved duct with two bends, with all three ducts engraved in the flat top surface of the flat plate.
Figure 9B:
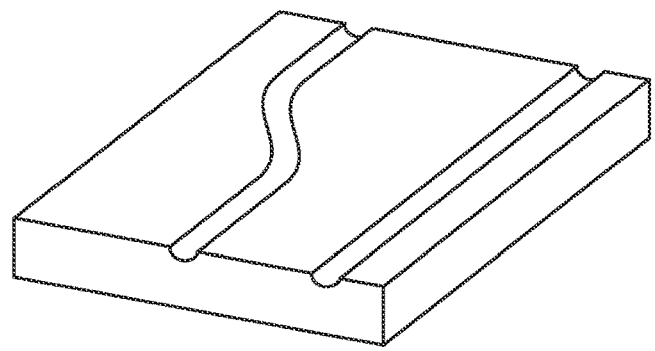
FIG. 9B shows another example of a flat plate with one straight duct and one curved duct with two bends engrooved in the flat top surface of the flat plate.
Figure 10:
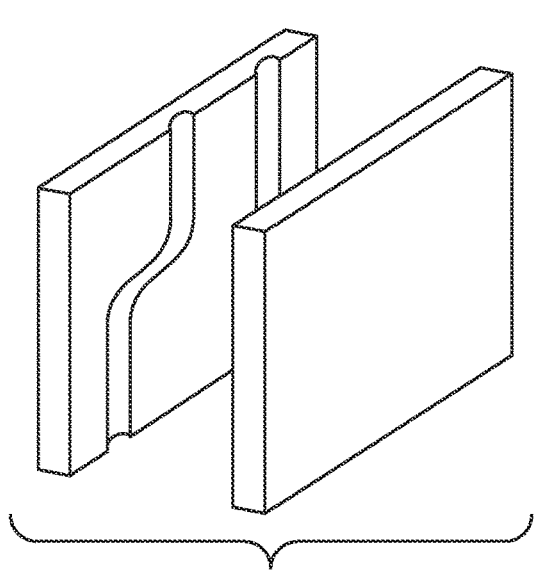
FIG. 10 shows two flat plates such as shown in FIG. 9B facing each other and ready to mate with one another and engrooved as the mirror images of each other such as shown in FIG. 9B.
Figure 11A:
FIG. 11A shows a side view of a plate that is not completely flat but that has a bend in a middle section thereof so as to have two flat portions in different parallel planes.
Figure 11B:
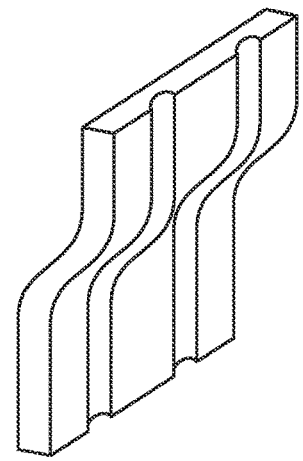
FIG. 11B shows the plate of FIG. 11A in a perspective view that also shows two ducts in a surface thereof.
Figure 12A:
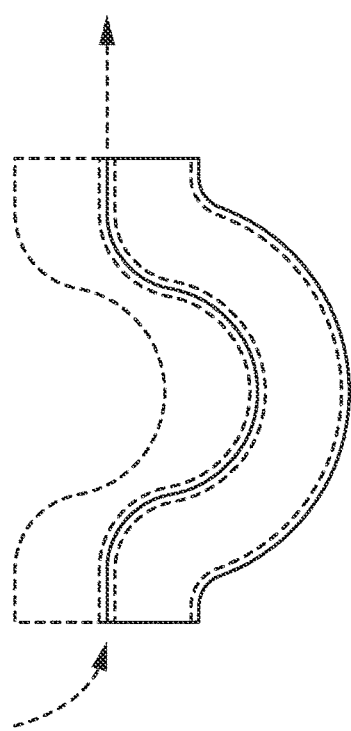
FIG. 12A shows two non-flat mating plates that are almost completely curved with a pronounced bend in the middle sections thereof so as to have two short end portions at inlet and outlet ends thereof.
Figure 12B:
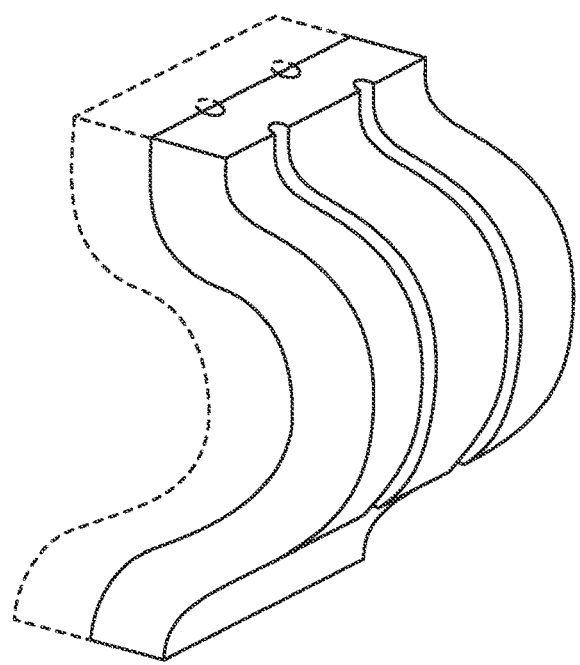
FIG. 12B shows the plates of FIG. 12A in a perspective view that also shows two ducts shown engraved in a surface thereof.
Figure 12C:
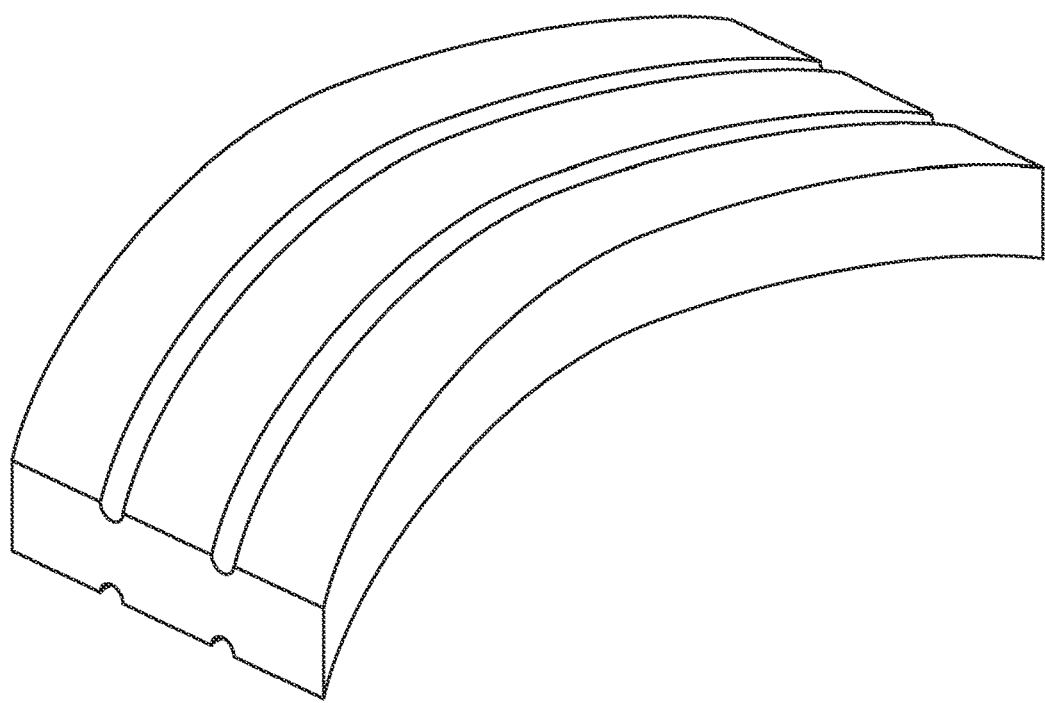
FIG. 12C shows a flat curved plate with similarly curved ducts engrooved in parallel.
Figure 13:
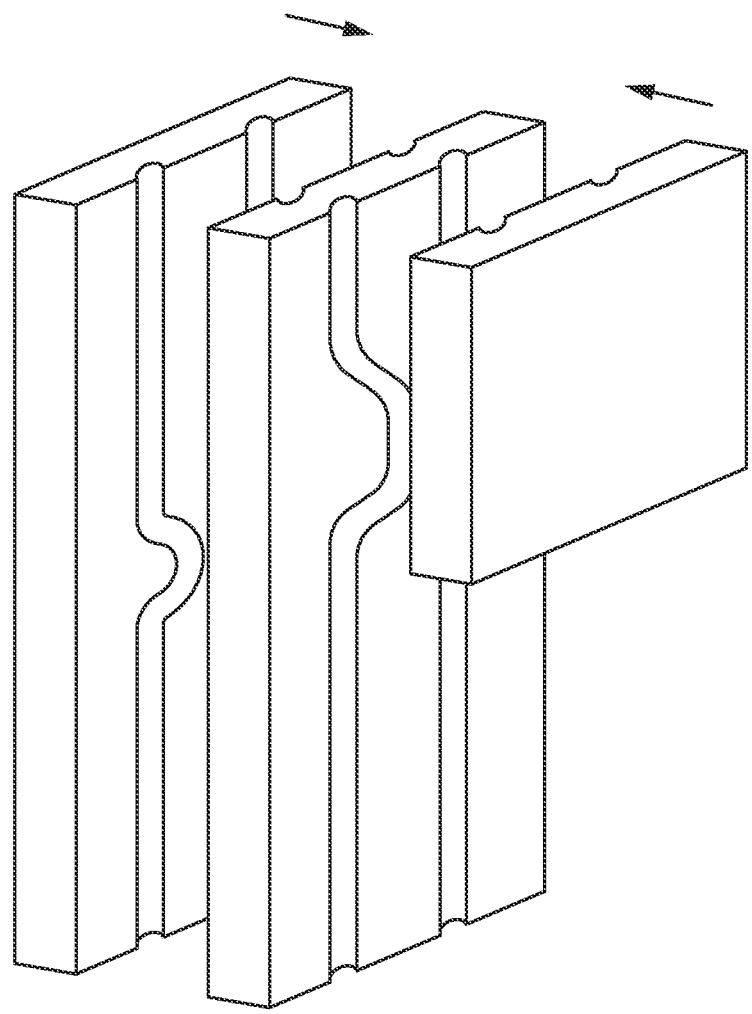
FIG. 13 shows two mating plates of similar dimensions and a third plate with different dimensions with partial mirroring so as to form ducts allowing for a different assembly within the same assembly.

FIG. 8 shows a view of a purifier attached to the internal side of a vehicle door to purify the air of the vehicle.

As shown in the various figures described above, the invention allows for multiple plaques or plates to be assembled and used to provide multiple full ducts for receiving air at an inlet, heating and thereby purifying the air as it passes through the ducts, and providing purified air through an outlet as the air exits the ducts.

Previous air purifiers of the applicant always kept a minimum height of the vertical ducts to allow enough fluid residence time for the microorganism to be incinerated.

The present invention permits the height of the applicant's prior art purifiers to be reduced by providing a duct design with at least one curve as in FIG. 1A thus maintaining the duct length, though serpentine, to acquire enough residence time for microorganism destruction.

The present invention also allows for longer or shorter, thinner or thicker air purifiers, depending on the size of each plate and how many plates are assembled.

In FIG. 9A a combination of three ducts or portions of ducts engraved in a plate is shown with a longer length duct 105 with three bends, a shorter length duct 101 with one bend, and a straight duct 102 allowing multiple residence time options, i.e. longer, intermediate, and shorter residence times, respectively.

As shown in FIG. 9B, the present invention also allows one plaque or plate to have straight and curved formed ducts suited the same for two different heating systems in the same plaque or plate when for instance a forced air flow is used requiring longer ducts to maintain the gas residence time within the duct and another with a shorter path, operating by convection.

FIG. 10 shows a plate similar to that shown in FIG. 9B on the left facing in a direction ready to mate with a flat plate with a mirror i on the right.

FIG. 11A shows a side view of a plate not necessarily flat. The bend is such that there are two flat portions lying in parallel planes joined together by a bend portion of the plate. FIG. 11B shows the plate of FIG. 11A with the bend portion in a perspective view wherein the two flat portions can be seen as forming a stepped configuration for the plate. There are two half-ducts shown in this example and extend in a straight line from end-to-end. But these may instead have an irregular course such as the ducts 101, 105 with bends as in FIG. 9A. In that case, there would be a stepped plate with ducts having bends traversing the stepped plate.

FIG. 12A shows a side view of another variation of an assembly of curved plates made for instance as shown in perspective by the two curved plates of FIG. 12B. The plates are in this case bent to have a hump in the middle portion with end portions at the same level. The mating surfaces are curved and as such provide curved ducts engrooved therein. A flat curved plate is shown in FIG. 12C with half-ducts that are curved. In this case, mating surfaces will lie in the same plane. Although shown with grooves engraved in both top and bottom surfaces of the plate, it should be realized that for some purposes the grooves may be absent on one surface.

In FIGS. 11A, 11B, 12A, 12B and 12C, the plate itself is bent at least one time, so that when assembled together with a similar bent plate a first duct is formed partially or in full either end-to-end straight or with at least a portion of the duct with a curve therein. If the duct is provided with a curve, a second channel or duct may be added that is end-to-end straight so that when assembled together with a similar open half-duct in the facing plate a second duct is formed in full as a straight duct. The end-to-end course of the one or more ducts shown in FIG. 12C may be configured to be uniformly curved in a way that matches the curve of the bend in the plate.

FIG. 13 shows that in a stack of plates the interfaces can have different configurations of ducts and do not necessarily have to have the same, uniform configuration throughout as shown in other embodiments above. Even the plate sizes may vary within a stack, depending on the application as shown by the rightmost plate.

A plate such as shown in FIG. 1A may be made of a ceramic material for assembly adjacent a facing plate of ceramic material such as shown in FIGS. 1B, 1C, and 2, 5 and 6 as a pair or as an assembly of plates to form a mass or block of ceramic material for the sterilization of air in a duct or ducts formed in the assemblage of plates. At least one of each pair of facing plates has an open channel in a surface of the plate such that when the plate and the facing plate are assembled face-to-face with a tight interface the open channel forms at least a part of the duct. A heating element threaded as shown in FIG. 4A and FIG. 4B or by a resistive wire type structure as in FIG. 4C that resides in the duct is energizable by at least one electrical power source such as a DC or AC source and when energized heats air or some other gas in need of sterilization within the duct to a very high temperature, for instance to over 100° C. before the heated gas escapes by convection from inside the at least one duct.

The assembled pair of plates may be attached to an interior of a container of an air sterilization apparatus with at least one air inlet and at least one air outlet.

The open channel may have at least one portion with a curve therein so that when assembled together with a similarly curved open channel in the facing plate the duct is formed in full with at least a portion of the duct with a curve therein.

The open channel may be straight so that when assembled together with a similarly straight open channel in the facing plate the duct is formed in full as a straight duct.

The plate may have more than one open channel therein with a first channel having at least one portion with a curve therein so that when assembled together with a similarly curved open channel in the facing plate a first duct is formed in full with at least a portion of the duct with a curve therein and wherein a second channel is straight so that when assembled together with a similarly straight open channel in the facing plate a second duct is formed in full as a straight duct.

The plate may be flat as in FIGS. 1A, 9A, and 9B for example, curved as in FIGS. 12A and 12B, or curved in part and flat in part as shown in FIGS. 11A and 11B, or a flat curved plate as shown in FIG. 12C.

The new air sterilizing plaque/plate assembly 110 formed for example of just two plaques/plates 100, can be as thin as 5 mm allowing for its incorporation to a new range of air purifiers as shown for example in FIGS. 7 and 8 but also to be added to a picture frame, one piece of furniture or a car door as seen in FIG. 8. The aim is to reduce airborne viruses, fungi, bacteria and other microorganisms with such an air purifier located within the confines of a habitable living space or vehicle. The stacked approach is unique in providing for design flexibility to meet different applications without having to redesign an entire block sized and drilled for the given application.

The new assembly allows for instance for a lengthy thin system with just two plaques or a short and thick assembly with multiple plaques/plates, both with same air sterilizing capacity.

Also the new assembly with straight, curved and even shorter formed ducts allows for different set ups, for instance shorter ducts when gas flows in by convection, longer ducts when there is a forced gas flow. As in the previous patents of the applicant, the flow of gas is guaranteed by convection when the sterilizing ducts of the plaque or plate assemblies are positioned in a substantially vertical position and the ducts are heated by a resistive wire to reach a selected high temperature such as at least 100° C., creating a chimney type of effect for convection of contaminated air or other gas.

The air or other gas is sterilized when exposed to heat during the required residence time inside the ducts and then cooled by release or by an optional heat exchanger.

Thus, a mass or block of material such as ceramic is formed by at least two plaques or plates with at least one half duct and preferably two matching half ducts to form full ducts of small diameter when attached together. These ducts are preferably heated by at least one electrically resistant wire that passes through each duct jointly or separately controlled. The resistant wire is connected to a power supply. When power runs through the wire, the resistance of the wire generates heat, which is radiated into the air surrounding the wire inside the duct. The assembly of power supply and resistant wire is designed to provide heat inside said ducts in excess of 100° Celsius. The heat inside the ducts, when the resistant wire is plugged into an exterior power source generates an air up stream by means of heating the air there contained when the ducts in the ceramic or other nonconductive material are in its preferably vertical position. When said heated air exits the ducts a negative pressure is created at the bottom of the ducts dragging exterior air into the ceramic ducts and therefore creating a continuous air circulation through the ducts. Airborne micro-organisms are exterminated by heat when passing inside the heated ducts. The continuous airflow generated by the air convection as above described assures 99.99% air sterilization in a quiet and efficient way and with low power consumption. The tubes are preferably made of a good quality ceramic or equivalent insulated material that can stand heat well above 200° C. and allow the ducts to be as close as possible to allow heat interchange between them. The ceramic core or block is inserted into an exterior casing equipped with easy air access at the bottom. An optional heat exchanger can be used at some distance over the air exhausting top of the ceramic ducts and a casing to be made of a material resistant to impact and heat, with at least one air outlet that will preferably boost air speed out. The casing is preferably constructed to incorporate the ceramic core and can be structured to be attached internally or externally to a device where air will circulate with or without a fan attached. It should also be realized that variations in the manner of heating the ducts are contemplated. For instance, the same duct may be heated at different times or at the same time to achieve different levels of heat. In such cases different heating elements may be connected to corresponding straight and nonstraight ducts. It should also be realized that the sterilization system may be configured to work in different directions, depending on how it is placed or oriented in service.

It will also be understood that the following claims are intended to cover all of the generic and specific features of the invention herein described and that all statements of the scope of the invention which, as a matter of language, might be said to fall therebetween.

What is claimed is:

1. A sterilization system for the sterilization of gas in one or more ducts, comprising:

at least two stacked plates, wherein at least one plate of the at least two stacked plates has an engraved portion, wherein the at least two stacked plates form a stacked plate pair that together with the engraved portion of the at least one plate form the one or more ducts, resulting in a gas sterilization assembly with the ono or more ducts having at least one heating element residing therein that when supplied with an electric current heats gas within the one or more ducts to over 100° C. before the gas escapes by convection from inside the one or more ducts.

2. The sterilization system of claim 1, wherein the engraved portion of the at least two stacked plates incorporates straight, or non straight, or both straight and non straight engraved plates incorporate straight, or non straight, or both straight and non straight engraved portions.

3. The sterilization system of claim 2, wherein the one or more ducts comprise a plurality of ducts with a corresponding plurality of heating elements residing therein that are controlled separately.

4. The sterilization system of claim 1, wherein the gas sterilization assembly is in a container or in a space formed inside a wall, a lamp, a piece of furniture, or a vehicle.

5. The sterilization system as claimed in claim 4, wherein the system is configured such that gas in the form of contaminated air flows into the one or more ducts by air convection, the gas sterilization assembly having at least one bottom inlet at a lower level under the one or more ducts and at least one top outlet at an upper level above the one or more ducts allowing hot air to exit freely upwards generating a negative pressure at the at least one bottom inlet forcing the contaminated air upwards into the at least one duct and out through the at least one top outlet in a continuous and constant flow of air.

6. The sterilization system as claimed in claim 1, wherein each plate of the at least two plates includes an engraved portion that has at least one curve engraved therein so that when assembled together a curved duct is formed.

7. The sterilization system as claimed in claim 1, wherein a fan is coupled to the gas sterilization assembly to enhance air movement in the sterilization system in order to improve sterilized gas production.

8. The sterilization system as claimed in claim 1, wherein the sterilization system is incorporated into a ventilation duct in a ventilation system for a space in a building.

9. The sterilization system as claimed in claim 1, wherein the gas sterilization assembly is contained within an insulated cover to inhibit radiation of heat outside the gas sterilization assembly so as to concentrate heat inside the one duct one or more ducts.

10. The sterilization system as claimed in claim 1, wherein at least one filter or particle remover with or without HEPA or carbon filters is coupled to the gas sterilization assembly, attached or not to a fan.

11. The sterilization system as claimed in claim 1, wherein the sterilization system is monitored and operated by means of wireless communication.

12. A plate comprising a ceramic material for assembly adjacent a facing plate of ceramic material as an assembled pair of plates to form a mass or block for the sterilization of a gas in a duct formed in the mass or block, the plate having an open channel in a surface of the plate such that when the plate and the facing plate are assembled face-to-face the open channel forms at least a part of the duct, wherein at least one heating element provided in the duct is energizable and when energized heats the gas within the duct to over 100° C. before the heated gas escapes by convection from inside the duct.

13. The plate as claimed in claim 12, wherein the mass or block comprising the assembled pair of plates is attached to an interior of a container of a gas sterilzation apparatus with at least one gas inlet and at least one gas outlet.

14. The plate as claimed in claim 12, wherein the open channel has at least one portion with a curve therein so that when assembled together with a similarly curved open channel in the facing plate the duct is formed with at least a portion of the duct with a curve therein.

15. The plate as claimed in claim 12, wherein the open channel is straight so that when assembled together with a similarly straight open channel in the facing plate the duct is formed as a straight duct.

16. The plate as claimed in claim 15, wherein the plate has more than one open channel with a first open channel having at least one portion with a curve therein so that when assembled together with a similarly curved open channel in the facing plate a first duct is formed with at least a portion of the duct with a curve therein and wherein a second open channel is straight so that when assembled together with a similarly straight open channel in the facing plate a second duct is formed as a straight duct.

17. The plate of claim 12, wherein the plate is flat, curved, or curved in part and flat in part.

18. The plate of claim 12, wherein the plate is bent at least one time so that the plate is a bent plate and the surface is a curved surface, and the open channel has a bent course running between edges of the curved surface of the bent plate such that the bent course runs from one end of the bent plate to another end.

19. The plate of claim 12, wherein said plate is a curved plate with said open channel comprising at least one curved channel engraved in said surface of the curved plate parallel to edges of the curved plate.

20. The plate of claim 12, wherein the surface of the plate is flat, curved, or curved in part and flat in part.

21. A gas sterilization apparatus comprising the plate according to claim 12.

\* \* \* \* \*